United States Patent [19]
Scanlan et al.

[11] Patent Number: 5,883,294
[45] Date of Patent: Mar. 16, 1999

[54] SELECTIVE THYROID HORMONE ANALOGS

[75] Inventors: Thomas S. Scanlan; Grazia Chiellini; Hikari Yoshihara, all of San Francisco; James Apriletti, Berkeley; John D. Baxter; Ralff C. J. Ribeiro, both of San Francisco, all of Calif.

[73] Assignee: The Regeants of the University of California, Calif.

[21] Appl. No.: 877,792

[22] Filed: Jun. 18, 1997

[51] Int. Cl.$^6$ ..................................................... C07C 59/56
[52] U.S. Cl. .............................. 562/471; 560/52; 560/57; 560/61; 560/9; 562/426; 562/460; 562/464; 514/543; 514/570
[58] Field of Search .................... 562/471, 426, 562/460, 464; 560/52, 57, 61, 9; 514/543, 570

[56] References Cited

U.S. PATENT DOCUMENTS

| 4,323,691 | 4/1982 | Ours et al. | 560/36 |
| 4,714,897 | 12/1987 | Andrews et al. | |
| 4,766,121 | 8/1988 | Ellis et al. | |

FOREIGN PATENT DOCUMENTS

95/05358  2/1995  WIPO.

OTHER PUBLICATIONS

Taylor, A.H., Stephan, Z.F., Steele, R.E. & Wong, N.C.W., "Beneficial effects of a novel thyromimetic on lipoprotein metabolism," Mol. Pharmacol., vol. 52:542–547 (1997).
Underwood, A.H., et al., & Shah, V.P., "A thyromimetic that decreases plasma cholesterol levels without increasing cardiac activity," Nature, vol. 324:425–429 (1986).
Yokoyama, N., et al. & Steels, R.E., Synthesis and structure–activity relationships of oxamic acid and acetic acid derivatives related to L–thyronine., J. Med. Chem., vol. 38:695–707 (1995).
Dietrich W.S. et al., "Thyroxine Analogues. 23. Quantitative Structure–Activity Correlation Studies of in Vivo and in Vitro Thyromimetic Activities," Journal of Medicinal Chemistry, vol. 20(7):863–880 (1977).
Jorgensen C.E. et al., "Thyroxine Analogs. 22. Thyromimetic Activity of Halogen–Free Derivatives of 3,5–Dimethyl–L–thyronine," Journal of Medicinal Chemistry, vol. 17(4):434–439 (1974).
Leeson D.P. et al., "Selective Thyromimetics. Cardiac–Sparing Thyroid Hormone Analogues Containing 3'–Arylmethyl Substituents," J. Med. Chem., vol. 32(2):320–336 (1989).
Leeson D.P. et al., "Thyroid Hormone Analogues. Synthesis of 3'–Substituted 3,5–Diiodo–L–thyronines and Quantitative Structure–Activity Studies of in Vitro and in Vivo Thyrominetic Activities in Rat Liver and Heart," J. Med. Chem., vol. 31:37–54 (1988).
Ribeiro R.C. et al., "Thyroid Hormone Export Regulates Cellular Hormone Content and Response," J. Biol. Chem., vol. 271:17147–17151 (1996).
Westerfield W.W. et al., "New Assay Procedure for Thyroxine Analogs," Endocrinology, vol. 77:802 (1965).

*Primary Examiner*—Paul J. Killos
*Attorney, Agent, or Firm*—Cooley Godward LLP

[57] ABSTRACT

Selective thyroid hormone agonists are disclosed that are highly selective for the TRβ subtype with high binding affinity. Methods of using such agonists and pharmaceutical compositions containing them are also disclosed, as are novel procedures for their preparation.

17 Claims, No Drawings

SELECTIVE THYROID HORMONE ANALOGS

INTRODUCTION

Technical Field

This invention relates to selective thyroid hormone agonists, methods of using such compounds, and pharmaceutical compositions containing them. The invention also relates to methods of preparing such compounds.

Background

Nuclear receptors represent a superfamily of proteins that specifically bind a physiologically relevant small molecule, such as hormone or vitamin. As a result of a molecule binding to a nuclear receptor, the nuclear receptor changes the ability of a cell to transcribe DNA, i.e. nuclear receptors modulate the transcription of DNA, although they may have transcription independent actions. Unlike integral membrane receptors and membrane associated receptors, the nuclear receptors reside in either the cytoplasm or nucleus of eukaryotic cells. Thus, nuclear receptors comprise a class of intracellular, soluble ligand-regulated transcription factors.

Nuclear receptors include receptors for thyroid hormones. Thyroid hormones promote normal growth and development and control an extraordinary number of regulatory functions in mammals. They regulate fetal development, cholesterol metabolism, the level of obesity, free radical formation, intestinal and cardiovascular functions, and bone and calcium metabolism. In current medical practice, thyroid hormones are used mostly for replacement therapy for humans with hypothyroidism, and to suppress the pituitary gland stimulation of the thyroid gland in patients with thyroid nodules or cancer. However, these hormones cannot be administered in high doses because of significant side effects, mainly on the heart.

There are two major subtypes of the thyroid hormone receptor, TRα and TRβ, and they are expressed from two different genes. Preliminary experiments indicate that the α and β subtypes are differentially expressed in various tissues. Observations suggest that the α-form of the receptors contribute in a substantial way to cardiac stimulating side effects, and that a β-selective agonist would be less likely to have this side effect.

It would be highly desirable to produce thyroid hormone agonists without the cardiac stimulating side effects. For example, they could then be used at higher doses for those purposes noted above, especially for lowering blood cholesterol levels, promoting weight reduction, treating diseases associated with an imbalance of thyroid hormones, for example osteoporosis and depression, and treatment of cardiac arrhythmia. Additionally, it would be desirable to find such compounds that are free of halogen, in particular the iodine that is found in the naturally occurring thyroid hormones, as it is believed to contribute to the undesirable side effects.

Surprisingly, a small class of halogen-free thyroid hormone agonists has been discovered, which are highly selective for the TRβ subtype with high binding affinity.

A previous disclosure of interest is U.S. patent application Ser. No. 08/764,870, filed Dec. 13, 1995, the complete disclosure of which is hereby incorporated by reference.

SUMMARY OF THE INVENTION

The present invention relates to compounds of Formula I:

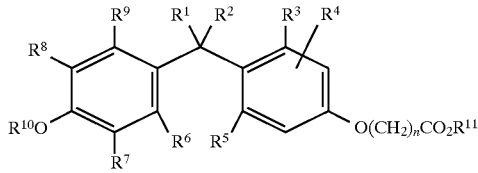

wherein:

n is 1, 2 or 3;

$R^1$ and $R^2$ are independently hydrogen or lower allyl; or $R^1$ and $R^2$ when taken together with the carbon to which they are attached represent —CHOH, —C=O or —C=S;

$R^3$ and $R^5$ are methyl;

$R^4$ is hydrogen, lower alkyl, or cycloalkyl;

$R^6$ and $R^9$ are hydrogen or lower alkyl;

$R^7$ and $R^8$ are independently hydrogen, lower alkyl, optionally substituted phenyl, optionally substituted benzyl, or heteroaryl;

with the proviso that $R^7$ and $R^8$ cannot both be hydrogen;

$R^{10}$ is hydrogen, lower alkyl, cycloalkyl, or acyl; and $R^{11}$ is hydrogen, lower alkyl, or cycloalkyl;

and the pharmaceutically acceptable salts thereof.

In a second aspect, the invention relates to a method of treatment of mammals having a disease state that is treatable by selective thyroid hormones, comprising administering a therapeutically effective dose of a compound of Formula I.

In a third aspect, the invention relates to a pharmaceutical composition containing a therapeutically effective amount of a compound of Formula I admixed with at least one pharmaceutically acceptable excipient.

In a fourth aspect, the invention relates to processes for preparing the compounds of Formula I.

DETAILED DESCRIPTION OF THE INVENTION

Definitions

As used herein:

"Alkyl" means a branched or unbranched saturated monovalent hydrocarbon radical containing 1 to 8 carbon atoms, such as methyl, ethyl, propyl, tert-butyl, n-hexyl, n-octyl and the like.

"Lower alkyl" means a branched or unbranched saturated monovalent hydrocarbon radical containing 1 to 6 carbon atoms, such as methyl, ethyl, propyl, isopropyl, tert-butyl, butyl, n-hexyl and the like, unless otherwise indicated.

"Cycloalkyl" as used herein means a saturated monovalent monocyclic hydrocarbon radical containing 3–8 carbon atoms, such as cyclopropyl, cyclobutyl, cyclopentyl, cyclohexyl, cycloheptyl and cyclooctyl.

"Lower alkoxy" means the group —O—(lower alkyl) wherein lower alkyl is as herein defined.

"Halo" or "halogen" means fluoro, chloro, bromo, or iodo.

The term "aryl" refers to a monovalent unsaturated aromatic carbocyclic radical having a single ring (e.g., phenyl) or two rings (e.g., naphthyl or biphenyl), which can optionally be mono-, di- or tri-substitated, independently, with OH, COOH, lower alkyl, lower alkoxy, nitro, amino, alkylamino, dialkylamino, trifluoromethyl and/or cyano.

The term "heteroaryl" refers to a monovalent aromatic carbocyclic radical having 1–3 heteroatoms within a single ring, (e.g., pyridyl, imidazolyl, thiazolyl, pyrimidine, oxazolyl, and the like), which can optionally be mono-, di- or tri-substituted, independently, with OH, COOH, lower alkyl, lower alkoxy, nitro, amino, alkylamino, dialkylamino, trifluoromethyl and/or cyano.

The term "heteroatom" refers to oxygen, sulfur and nitrogen, unless otherwise specified.

The term "acyl" refers to the group —C(O)R, where R is lower alkyl or cycloalkyl, for example acetyl, propionyl, cyclopropionyl, butanoyl, and the like.

"Optional" or "optionally" means that the subsequently described event or circumstance may or may not occur, and that the description includes instances where said event or circumstance occurs and instances in which it does not. For example, optionally substituted phenyl indicates either unsubstituted phenyl, or phenyl mono-, di- or tri-substituted, independently, with OH, COOH, lower alkyl, lower alkoxy, halo, nitro, amino, alkylamino, dialkylamino, trifluoromethyl and/or cyano.

As used herein, the terms "inert organic solvent" or "inert solvent" mean a solvent inert under the conditions of the reaction being described in conjunction therewith [including, for example, benzene, toluene, acetonitrile, tetrahydrofuran ("THF"), dimethylformamide ("DMF"), chloroform ("CHCl$_3$"), methylene chloride (or dichloromethane or "CH$_2$Cl$_2$"), diethyl ether, ethyl acetate, acetone, methylethyl ketone, methanol, ethanol, propanol, isopropanol, tert-butanol, dioxane, pyridine, and the like]. Unless specified to the contrary, the solvents used in the reactions of the present invention are inert solvents.

"Pharmaceutically acceptable salt" means those salts which retain the biological effectiveness and properties of the compounds of Formula I, and which are not biologically or otherwise undesirable. Such salts may be prepared from inorganic and organic bases. Salts derived from inorganic bases include, but are not limited to, the sodium, potassium, lithium, ammonium, calcium, and magnesium salts. Salts derived from organic bases include, but are not limited to, salts of primary, secondary and tertiary amines, substituted amines including naturally-occurring substituted amines, and cyclic amines, including isopropylamine, trimethylamine, diethylamine, triethylamine, tripropylamine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, and N-ethylpiperidine. It should also be understood that other carboxylic acid derivatives would be useful in the practice of this invention, for example carboxylic acid amides, including carboxamides, lower alkyl carboxamides, di(lower alkyl) carboxamides, and the like.

It should be understood that Formula I as drawn is intended to represent the racemic form of compounds of Formula I as well as the individual enantiomers and non-racemic mixtures thereof, although for the sake of clarity only one enantiomer is shown. The scope of the invention as described and claimed encompasses the racemic forms of the compounds of Formula I as well as the individual enantiomers and non-racemic mixtures thereof.

The term "treatment" as used herein covers any treatment of a disease in a mammal, particularly a human, and includes:

(i) preventing the disease from occurring in a subject which may be predisposed to the disease but has not yet been diagnosed as having it;

(ii) inhibiting the disease, i.e. arresting its development; or (iii) relieving the disease, i.e. causing regression of the disease.

The term "disease state which is alleviated by treatment with a thyroid hormone agonist" as used herein is intended to cover all disease states which are generally acknowledged in the art to be usefully treated with thyroid hormone agonists in general, and those disease states which have been found to be usefully treated by the specific thyroid hormone agonists of our invention, the compounds of Formula I. Such disease states include, but are not limited to, hypercholesterolemia, obesity, loss of bone and calcium through metabolism, cardiac arrhythmia, hypothyroidism, compromised cardiac function, atherosclerosis, and pituitary gland stimulation of the thyroid gland in patients with thyroid nodules or cancer.

The term "therapeutically effective amount" refers to that amount which is sufficient to effect treatment, as defined above, when administered to a mammal in need of such treatment. The therapeutically effective amount will vary depending on the subject and disease state being treated, the severity of the affliction and the manner of administration, and may be determined routinely by one of ordinary skill in the art.

Appendix 1 is an appendix of references.

METHODS OF TREATMENT

The compounds of Formula I can be useful in medical treatments and exhibit biological activity which can be demonstrated in the following tests:

(i) the induction of mitochondrial α-glycerophosphate dehydrogenase (GPDH:EC 1.1.99.5). This assay is particularly useful since in certain species e.g. rats it is induced specifically by thyroid hormones and thyromimetics in a close-related manner in responsive tissues e.g. liver, kidney and the heart (Westerfield, W. W., Richert, D. A. and Ruegamer, W. R., Endocrinology, 1965, 77, 802). The assay allows direct measurement in rates of a thyroid hormone-like effect of compounds and in particular allows measurement of the direct thyroid hormone-like effect on the heart;

(ii) the elevation of basal metabolic rate as measured by the increase in whole body oxygen consumption;

(iii) the stimulation of the rate of beating of atria isolated from animals previously dosed with thyromimetics;

(iv) the change in total plasma cholesterol levels as determined using a cholesterol oxidase kit (for example, the Merck CHOD iodine colourimetric kit);

(v) the measurement of LDL (low density lipoprotein) and HDL (high density lipoprotein) cholesterol in lipoprotein fractions separated by ultracentrifugation; and p (vi) the change in total plasma triglyceride levels as determined using enzymatic color tests; for example the Merck System GPO-PAP method.

The compounds of Formula I can be found to exhibit selective thyromimetic activity in these tests, (a) by increasing the metabolic rate of test animals, and raising hepatic GPDH levels at doses which do not significantly modify cardiac GPDH levels.

(b) by lowering plasma cholesterol and triglyceride levels, and the ratio of LDL to HDL cholesterol at doses which do not significantly modify cardiac GPDH levels.

The compounds of Formula I may therefore be used in therapy, in the treatment of conditions which can be alleviated by compounds which selectively mimic the effects of thyroid hormones in certain tissues whilst having little or no direct thyromimetic effect on the heart. For example, compounds of Formula I which raise hepatic GPDH levels and metabolic rate at doses which do not significantly modify cardiac GPDH levels are indicated in the treatment of obesity.

Compounds of Formula I which lower total plasma cholesterol, the ratio of LDL-cholesterol to HDL-cholesterol and triglyceride levels at doses which do not significantly modify cardiac GPDH levels are indicated for use as general antihyperlipidaemic (antihyperlipoproteinaemic) agents i.e. in the treatment of patients having elevated plasma lipid (cholesterol and triglyceride) levels. In addition, in view of this effect on plasma cholesterol and triglyceride, they are also indicated for use as specific anti-hypercholesterolemic and anti-hypertriglyceridaemic agents.

Patients having elevated plasma lipid levels are considered at risk of developing coronary heart disease or other manifestations of atherosclerosis as a result of their high plasma cholesterol and/or triglyceride concentrations. Further, since LDL-cholesterol is believed to be the lipoprotein which induces atherosclerosis, and HDL-cholesterol believed to transport cholesterol from blood vessel walls to the liver and to prevent the build up of atherosclerotic plaque, anti-hyperlipidemic agents which lower the ratio of LDL-cholesterol to HDL cholesterol are indicated as anti-atherosclerotic agents, herein incorporated by reference U.S. Pat. Nos. 4,826,876 and 5,466,861.

In addition, compounds of Formula 1 may be indicated in thyroid hormone replacement therapy in patients with compromised cardiac function.

In therapeutic use the compounds of the present invention are usually administered in a standard pharmaceutical composition.

The present invention therefore provides in a further aspect pharmaceutical compositions comprising a compound of Formula 1 or a pharmaceutically acceptable salt thereof and a pharmaceutically acceptable carrier. Such compositions include those suitable for oral, parenteral or rectal administration.

PHARMACEUTICAL COMPOSITIONS

Compounds of Formula 1 and their pharmaceutically acceptable salts which are active when given orally can be formulated as liquids for example syrups, suspensions or emulsions, tablets, capsules and lozenges.

A liquid composition will generally consist of a suspension or solution of the compound or pharmaceutically acceptable salt in a suitable liquid carrier(s), for example ethanol, glycerine, sorbitol, non-aqueous solvent such as polyethylene glycol, oils or water, with a suspending agent, preservative, surfactant, wetting agent, flavoring or coloring agent. Alternatively, a liquid formulation can be prepared from a reconstitutable powder.

For example a powder containing active compound, suspending agent, sucrose and a sweetener can be reconstituted with water to form a suspension; and a syrup can be prepared from a powder containing active ingredient, sucrose and a sweetener.

A composition in the form of a tablet can be prepared using any suitable pharmaceutical carrier(s) routinely used for preparing solid compositions. Examples of such carriers include magnesium stearate, starch, lactose, sucrose, microcrystalline cellulose and binders, for example polyvinylpyrrolidone. The tablet can also be provided with a color film coating, or color included as part of the carrier(s). In addition, active compound can be formulated in a controlled release dosage form as a tablet comprising a hydrophilic or hydrophobic matrix.

A composition in the form of a capsule can be prepared using routine encapsulation procedures, for example by incorporation of active compound and excipients into a hard gelatin capsule. Alternatively, a semi-solid matrix of active compound and high molecular weight polyethylene glycol can be prepared and filled into a hard gelatin capsule; or a solution of active compound in polyethylene glycol or a suspension in edible oil, for example liquid paraffin or fractionated coconut oil can be prepared and filled into a soft gelatin capsule. Compound of Formula 1 and their pharmaceutically acceptable salts which are active when given parenterally can be formulated for intramuscular or intravenous administration.

A typical composition for intramuscular administration will consist of a suspension or solution of active ingredient in an oil, for example arachis oil or sesame oil. A typical composition for intravenous administration will consist of a sterile isotonic aqueous solution containing, for example active ingredient, dextrose, sodium chloride, a co-solvent, for example polyethylene glycol and, optionally, a chelating agent, for example ethylenediamine tetracetic acid and an anti-oxidant, for example, sodium metabisulphite. Alternatively, the solution can be freeze dried and then reconstituted with a suitable solvent just prior to administration.

Compounds of Formula I and their pharmaceutically acceptable salts which are active on rectal administration can be formulated as suppositories. A typical suppository formulation will generally consist of active ingredient with a binding and/or lubricating agent such as a gelatin or cocoa butter or other low melting vegetable or synthetic wax or fat.

Compounds of Formula 1 and their pharmaceutically acceptable salts which are active on topical administration can be formulated as transdermal compositions. Such compositions include, for example, a backing, active compound reservoir, a control membrane, liner and contact adhesive.

The typical daily dose of a compound of Formula 1 varies according to individual needs, the condition to be treated and with the route of administration. Suitable doses are in the general range of from 0.001 to 10 mg/kg bodyweight of the recipient per day.

Within this general dosage range, doses can be chosen at which the compounds of Formula 1 lower plasma cholesterol levels and raise metabolic rate with little or no direct effect on the heart. In general, but not exclusively, such doses will be in the range of from 0.5 to 10 mg/kg.

In addition, within the general dose range, doses can be chosen at which the compounds of Formula 1 lower plasma cholesterol levels and have little or no effect on the heart without raising metabolic rate. In general, but not exclusively, such doses will be in the range of from 0.001 to 0.5 mg/kg.

It is to be understood that the 2 sub ranges noted above are not mutually exclusive and that the particular activity encountered at a particular dose will depend on the nature of the compound of Formula 1 used.

Preferably, the compound of Formula 1 is in unit dosage form, for example, a tablet or a capsule so that the patient may self-administer a single dose. In general, unit doses contain in the range of from 0.05–100 mg of a compound of Formula 1. Preferred unit doses contain from 0.05 to 10 mg of a compound of Formula 1.

The active ingredient may be administered from 1 to 6 times a day. Thus daily doses are in general in the range of from 0.05 to 600 mg per day. Preferably, daily doses are in the range of from 0.05 to 100 mg per day. Most preferably from 0.05 to 5 mg per day.

METHODS OF PREPARATION

Compounds of Formula I are prepared from intermediates of formula (3) and (6), the preparation of which is shown below.

Preparation of Compounds of Formula (3)

Compounds of Formula (3) are prepared as shown below in Reaction Scheme I.

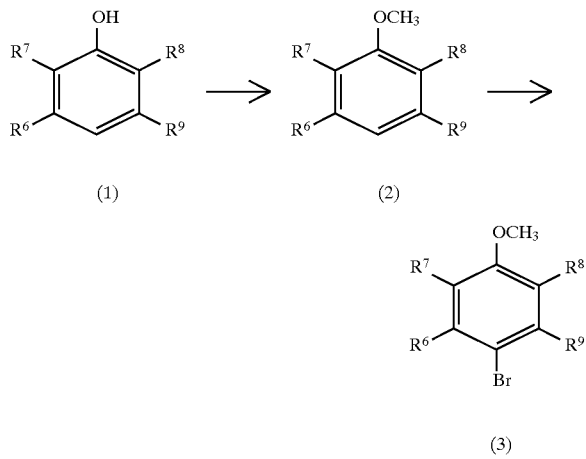

Compounds of Formula (1) are commercially available, or may be prepared by means well known in the art. In general, the phenol of Formula (1) is first protected by conversion to the methoxy derivative, for example by reacting (1) with methyl iodide in the presence of a base, for example potassium carbonate, in a polar solvent, for example N,N-dimethylformamide (DMF. When the reaction is substantially complete, the protected phenol of Formula (2) is isolated and purified by conventional means, preferably by flash chromatography.

Clearly, other conventional phenol protecting groups could be utilized instead of methoxy, for example a silyl protecting group, e.g. t-butyldimethylsilyloxy.

The compound of Formula (2) is then brominated using potassium bromide in the presence of a crown ether, for example 18-Crown-6, and an oxidizing agent, for example 3-chloroperoxy benzoic acid. The reaction is carried out in an inert solvent, preferably methylene chloride. When the reaction is substantially complete, the 4-bromo derivative of Formula (3) is isolated and purified by conventional means, preferably by flash chromatography.

Preparation of Compounds of Formula (6)

Compounds of Formula (6) are prepared as shown below in Reaction Scheme II.

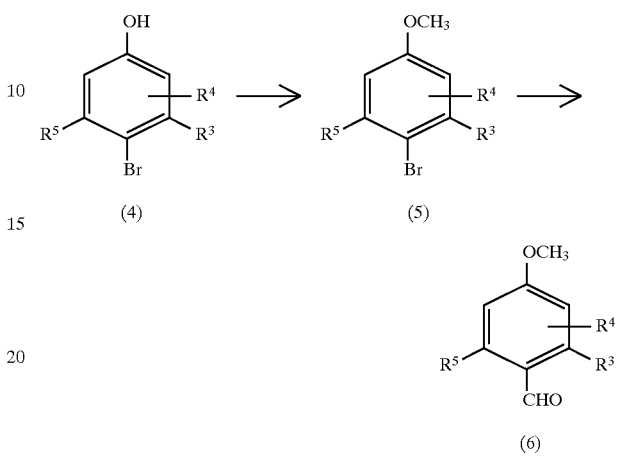

Compounds of Formula (4) are commercially available, or may be prepared by means well known in the art. In general, the phenol of Formula (4) is first protected by conversion to the methoxy derivative, or other conventional phenol protecting groups, as disclosed in Reaction Scheme I above, to give a p-bromo compound of Formula (5).

The bromo moiety of the compound of Formula (5) is then converted to a formyl group. The reaction is carried out conventionally, adding t-butyllithium to a solution of (5) in an inert solvent at about $-78°$ C., preferably tetrahydrofuran, and adding DMF to the cold solution. After stirring cold, the mixture is allowed to warm to room temperature. When the reaction is substantially complete, the 4-formyl derivative of Formula (6) is isolated and purified by conventional means, preferably by flash chromatography.

Preparation of Compounds of Formula I

Compounds of Formula I are prepared from (3) and (6) as shown below in Reaction Scheme III.

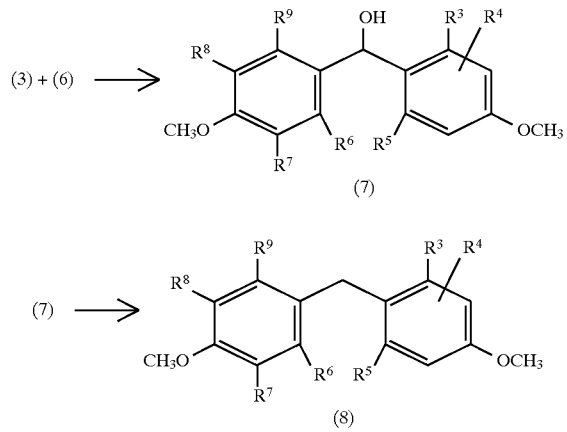

-continued
Reaction Scheme III

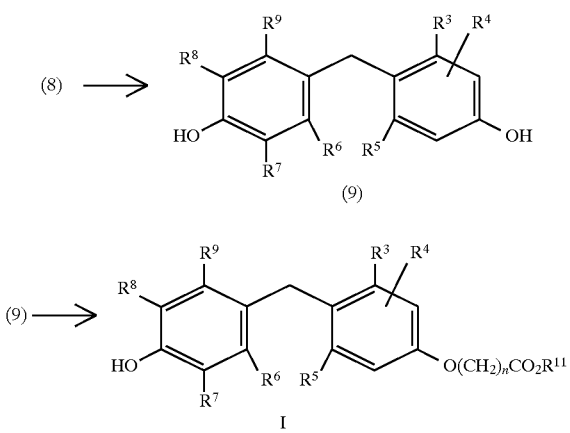

Compounds of Formula (7) are prepared by reaction of (3) and (6). In general, the p-bromo compound of Formula (3) is dissolved in an inert solvent, preferably tetrahydrofuran, cooled to about −78° C. and t-butyllithium added. After stirring for about 10 minutes, the compound of Formula (6) is added. After stirring cold, the mixture is allowed to warm to room temperature. When the reaction is substantially complete, the carbinol derivative of Formula (7) is isolated and purified by conventional means, preferably by flash chromatography.

The compound of Formula (7) is then hydrogenated to remove the hydroxy group. In general, a platinum or palladium catalyst is used, preferably palladium on carbon. The reaction is carried out in an acidic medium, preferably acetic acid in ethanol, under an atmosphere of hydrogen at room temperature and pressure. When the reaction is substantially complete, the compound of Formula (8) is isolated by conventional means, and preferably used with no further purification.

The dimethoxy derivative of Formula (8) is then demethylated. The reaction is carried out conventionally, using boron tribromide in methylene chloride. When the reaction is substantially complete, the dihydroxy derivative of Formula (9) is isolated and purified by conventional means, preferably by flash chromatography.

Preparation of I

The compound of Formula (9) is then converted to a compound of Formula I where $R^{10}$ is hydrogen by reaction with an ester of formula X—$(CH_2)_n$—$CO_2R^{11}$, where X is chloro, bromo or iodo, n is 1, 2 or 3, and $R^{11}$ is lower alkyl, for example t-butyl. The compound of Formula (9) is dissolved in an inert solvent, for example tetrahydrofuran, cooled to about −25° C., and cesium carbonate added followed by the halo ester. The mixture is stirred cold for about 1 hour, then allowed to warm to room temperature. When the reaction is substantially complete, the ester derivative of a compound of Formula I is isolated and purified by conventional means, preferably by flash chromatography. This ester is dissolved in a protic solvent, preferably methanol, and hydrolysed with a base, preferably sodium hydroxide. After acidification, the compound of Formula I is isolated and purified by conventional means.

Preparation of Compounds of Formula I

Compounds of Formula I where $R^1$ is other than hydrogen are prepared from compounds of Formula (7), as shown below in Reaction Scheme IV.

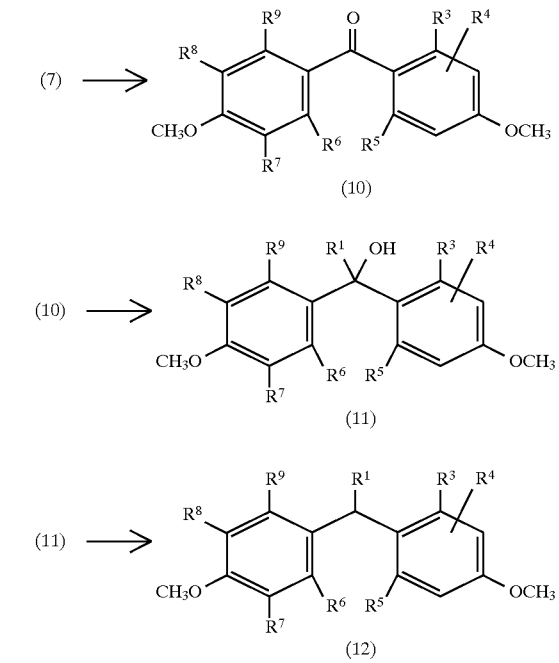

The ketones of Formula (10) are prepared from the carbinols of Formula (7) by oxidation. In general, the carbinol of Formula (7) is dissolved in an inert solvent, preferably methylene chloride, cooled to about 0° C., and an oxidizing agent, preferably pyridinium dichromate added. After stirring for about 4 hours, the ketone of Formula (10) is isolated and purified by conventional means, preferably by flash chromatography.

The compound of Formula (10) is then reacted with an organo cerium complex to give a compound of Formula (11). In general, anhydrous cerium chloride is stirred in an inert solvent preferably tetrahydrofuran, at room temperature for about 2 hours under an inert atmosphere. The resultant suspension is cooled to about −78° C. and an organolithium complex of formula $R^1Li$ added, and stirring continued for about 30 minutes, after which time the compound of Formula (10) in an inert solvent, preferably tetrahydrofuran, is added. The mixture is stirred for about 3 hours at −78° C., and warmed to 0° C. When the reaction is substantially complete, the compound of Formula (11) is isolated by conventional means, and preferably purified by column chromatography.

The compound of Formula (11) is then hydrogenated to the compound of Formula (12) in the same manner as shown for the conversion of (7) to (8) above.

The compound of Formula (12) is then treated with boron tribromide as shown above for the conversion of (8) to (9) above to give a 4,4'-dihydroxy derivative, which is converted to a compound of Formula I as shown above for the conversion of (9) to a compound of Formula I where $R^{10}$ is hydrogen by reaction with an ester of formula X—$(CH_2)_n$—$CO_2R^{11}$.

Preparation of Compounds of Formula I

Compounds of Formula I where $R^1$ and $R^2$ taken together with the carbon to which they are attached represent —C=O are prepared from compounds of Formula (10), as shown below in Reaction Scheme V.

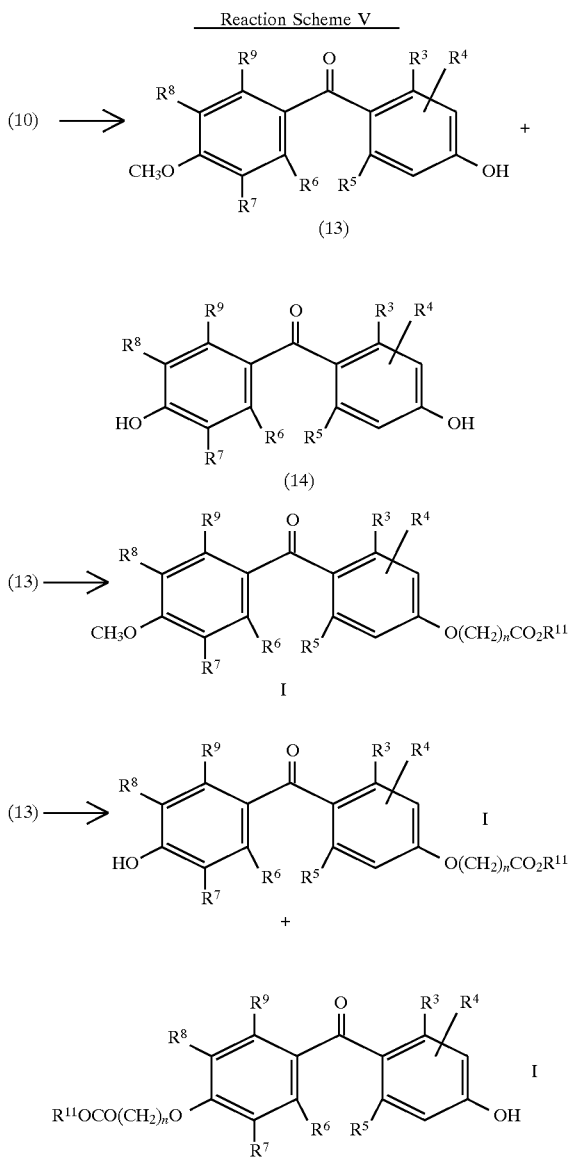

The ketone of Formula (10), prepared as shown above, is treated with boron tribromide in the same manner as shown above for the conversion of (8) to (9). A mixture of compounds is obtained, a 4,4'-dihydroxy compound (14), and a 4-hydroxy-4'-methoxy derivative (13).

The 4-hydroxy-4'-methoxy derivative (13) is then converted to a compound of Formula I where $R^{10}$ is methyl by reaction with an ester of formula X—$(CH_2)_n$—$CO_2R$, in the same manner as shown above for the conversion of (9) to a compound of Formula I. The 4,4'-dihydroxy compound (14), when subjected to the same conditions, gave a mixture of two compounds, a 4'-hydroxy-4-oxyalkanoic acid of Formula I and a 4-hydroxy-4'-oxyalkanoic acid of Formula I.

Preparation of Compounds of Formula I

Compounds of Formula I where $R^1$ and $R^2$ taken together with the carbon to which they are attached represent —C=O and $R^6$ is lower alkyl are prepared from compounds of Formula (10), as shown below in Reaction Scheme VI.

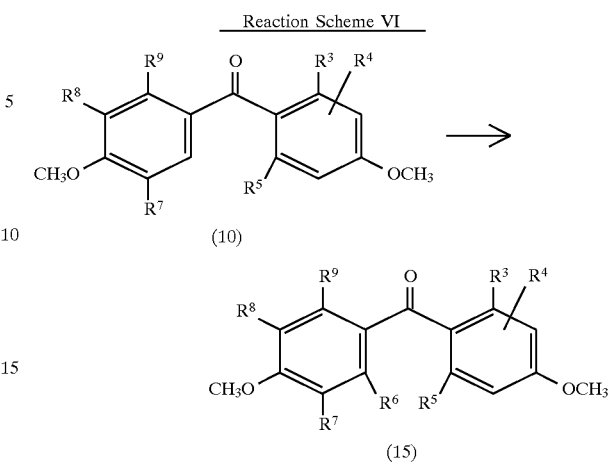

Anhydrous cerium chloride is reacted with an alkyl lithium, for example n-butyllithium, at about room temperature in an inert solvent, preferably tetrahydrofuran, to obtain a lithium cerium complex. The suspension thus obtained is cooled to about −78° C., and the ketone of Formula (10), prepared as shown above, is added. After about 3 hours at this temperature, followed by about 2 hours at 0° C., the compound of Formula (15) is isolated by conventional means, and preferably purified by flash chromatography.

The compound of Formula (15) is then treated with boron tribromide in the same manner as shown above for the conversion of (8) to (9), to yield a 4,4'-dihydroxy compound, which is converted to a compound of Formula I where $R^6$ is lower alkyl by reaction with an ester of formula X—$(CH_2)_n$—$CO_2R$, in the same manner as shown above for the conversion of (9) to a compound of Formula I, to give a mixture of three compounds; a 4'-hydroxy-4-oxyalkanoic acid of Formula I, a 4-hydroxy-4'-oxyalkanoic acid of Formula I, and a 4,4'-bis(oxyalkanoic acid) of Formula I.

Isolation and Purification of the Compounds

Isolation and purification of the compounds and intermediates described herein can be effected, if desired, by any suitable separation or purification procedure such as, for example, filtration, extraction, crystallization, column chromatography, thin-layer chromatography, thick-layer chromatography, preparative low or high-pressure liquid chromatography or a combination of these procedures. Specific illustrations of suitable separation and isolation procedures can be had by reference to the Examples hereinbelow. However, other equivalent separation or isolation procedures could, of course, also be used.

Separation of Enantiomers

The enantiomers of the compounds and intermediates described herein can be effected, if desired, by any conventional resolution means, for example by separation (e.g. fractional crystallization) of the diastereomeric salts formed by the reaction of a racemic compound of Formula I with an optically active base.

Salts of Compounds of Formula I

The compounds of Formula I where $R^{11}$ is hydrogen may be converted to a corresponding base addition salt from inorganic and organic bases by conventional means. Typically, the free acid of Formula I is dissolved in an inert organic solvent such as diethyl ether, ethyl acetate, chloroform, ethanol or methanol and the like, and the base added in a similar solvent. The temperature is maintained at 0°–50° C. The resulting salt precipitates spontaneously or may be brought out of solution with a less polar solvent.

The following preparation and examples illustrate the invention but are not intended to limit its scope.

EXAMPLE 1

Preparation of Compounds of Formula (2)
Preparation of (2) where $R^7$ is Isopropyl and $R^6$, $R^8$, and $R^9$ are Hydrogen A mixture of 2-isopropylphenol (1) (12.0 g, 88.1 mmol), methyl iodide (25.0 g, 176.2 mmol), and potassium carbonate (24.3 g, 176.2 mmol) in 44 mL of DMF was stirred for 20 hours at room temperature. The reaction mixture was diluted with 300 mL of ether and washed with 250 mL of water and 5×100 mL of brine. The organic portion was dried ($MgSO_4$), filtered, and evaporated to give an oil, which was purified by flash column chromatography (silica gel, 90:10 hexane/ethylacetate) to give 2-isopropylanisole (2) (12.5 g, 82.1 mmol, 93%); $^1$HNMR ($CDCl_3$) δ 1.2 (d, 6H), 3.3 (heptet, 1H), 3.8 (s, 3H), 6.8 (d, 1H), 6.88 (t, 1H), 7.13 (d, 1H), 7.2 (t, 1H).

Preparation of (2), Varying $R^6$, $R^7$, $R^8$, and $R^9$

In a similar manner, replacing 2-isopropylphenol with other compounds of Formula (1) and following the procedure described in Example 1 above, other compounds of Formula (2) are prepared.

EXAMPLE 2

Preparation of Compounds of Formula (3)
Preparation of (3) where $R^7$ is Isopropyl and $R^6$, $R^8$, and $R^9$ are Hydrogen To a suspension of potassium bromide (18.8 g, 157.7 mmol) in 400 mL of methylene chloride at 0° C. were added 18-Crown-6 (2.08 g, 7.88 mmol), 3-chloroperoxy benzoic acid (27.2 g, 157.7 mmol) and 2-isopropylanisole (12.0 g, 78.8 mmol). After stirring for 3 hours at 0° C., the reaction mixture was poured into ice water (500 mL), and stirred for 30 minutes. The organic layer was separated, washed with saturated $NaHCO_3$ solution (400 mL), followed by water (300 mL), and dried ($MgSO_4$). The solvent was evaporated to give an oil, which was purified by flash column chromatography (silica gel, 98:2 hexane/ethylacetate) to give 13 g (56.7 mmol, 72%) of 4-bromo-2-isopropylanisole (3) as an oil; $^1$HNMR ($CDCl_3$) δ 1.2 (d, 6H), 3.3 (heptet, 1H), 6.7 (d, 1H), 6.84 (d, 1H), 7.29 (s, 1H).

Preparation of (3), Varying $R^6$, $R^7$, $R^8$, and $R^9$

In a similar manner, replacing 2-isopropylanisole with other compounds of Formula (2) and following the procedure described in Example 2 above, other compounds of Formula (3) are prepared.

EXAMPLE 3

Preparation of Compounds of Formula (5)
Preparation of (5) where $R^4$ is Hydrogen and $R^3$ and $R^5$ are Methyl A mixture of 4-bromo-3,5-dimethylphenol (4) (25.0 g, 124.3 mmol), methyl iodide (35.3 g, 248.6 mmol), and potassium carbonate (34.4 g, 248.6 mmol) in 62.5 mL of DMF was stirred for 2 hours at room temperature. The reaction mixture was diluted with 300 mL of ether and washed with 250 mL of water and 5×100 mL of brine. The organic portion was dried ($MgSO_4$), filtered, and evaporated to give an oil, which was purified by flash column chromatography (silica gel, 90:10 hexane/ethylacetate) to give 4-bromo-3,5-dimethylanisole (5) (26 g, 120.8 mmol, 97%); $^1$HNMR ($CDCl_3$) δ 2.39 (s, 6H), 3.76 (s, 3H), 6.67 (s, 2H).

Preparation of (5), Varying $R^3$, $R^4$, and $R^5$

In a similar manner, replacing 4-bromo-3,5-dimethylphenol with other compounds of Formula (4) and following the procedure described in Example 3 above, other compounds of Formula (5) are prepared.

EXAMPLE 4

Preparation of Compounds of Formula (6)
Preparation of (6) where $R^4$ is Hydrogen and $R^3$ and $R^5$ are Methyl To 4-bromo-3,5-dimethylanisole (20 g, 93.0 mmol) in 500 mL of tetrahydrofuran at −78° C. was added 120 mL of tert-Butyllithium (1.7M in pentane). The reaction mixture was stirred for 30 minutes at −78° C. and then DMF (136.0 g, 186.0 mmol) was added. The reaction mixture was stirred for 1 hour at −78° C. and for 1.5 hours at room temperature, diluted with 300 mL of ether, washed with 300 mL of water, acidified 1N HCl, and 5×100 mL of brine. The organic portion was dried ($MgSO_4$), filtered, and evaporated to give the crude product, which was purified by flash column chromatography (silica gel, 90:10 hexane/ethylacetate) to yield 2,6-dimethyl-4-methoxybenzaldehyde (6), (9.50 g, 57.8 mmol, 62%) as a white solid; $^1$HNMR ($CDCl_3$ δ 2.61 (s, 6H), 3.83 (s, 3H), 6.6 (s, 2H), 10.5 (s, 1H).

Preparation of (6), Varying $R^5$

In a similar manner, replacing 4-bromo-3,5-dimethylanisole with other compounds of Formula (5) and following the procedure described in Example 4 above, other compounds of Formula (6) are prepared.

EXAMPLE 5

Preparation of Compounds of Formula (7)
Preparation of (7) where $R^4$, $R^6$, $R^7$ and $R^9$ are Hydrogen, $R^3$ and $R^5$ are Methyl, and $R^8$ is Isopropyl To 4-bromo-2-isopropylanisole (3) (12 g, 52.4 mmol) in 300 mL of tetrahydrofuran at −78° C. was added 68 mL of tert-Butyllithium (1.7M in pentane). The reaction mixture was stirred for 10 min at −78° C. and then 2,6-dimethyl-4-methoxybenzaldehyde (6) (8.6 g, 52.4 mmol) was added. The reaction mixture was stirred for 1 hour at −78° C. and for 1.5 hours at room temperature, diluted with 150 mL of ether, washed with 150 mL of water, acidified with 1N HCl, and washed with 5×50 mL of brine. The organic portion was dried ($MgSO_4$), filtered, and evaporated to give the crude product, which was purified by flash column chromatography (silica gel, 95:5 hexane/ethylacetate) to yield 3,5-dimethyl-4-(3'-isopropyl-4'-methoxybenzylhydroxy) anisole (7) (12 g, 38.2 mmol, 73%) as an oil; $^1$HNMR ($CDC_{13}$) δ 1.2 (dd, 6H), 2.27 (s, 6H), 3.30 (heptet, 1H), 3.80 (s, 6H), 6.26 (s, 1H), 6.59 (s, 2H) 6.76 (d, 1H), 6.89 (d, 1H), 7.24 (s, 1H).

Preparation of (7), Varying $R^4$, $R^6$, $R^7$, $R^8$ and $R^9$

In a similar manner, optionally replacing 4-bromo-2-isopropylanisole with other compounds of Formula (3), and optionally replacing 2,6-dimethyl-4-methoxybenzaldehyde with other compounds of Formula (6), and following the procedure described in Example 5 above, other compounds of Formula (7) are prepared.

EXAMPLE 6

Preparation of Compounds of Formula (8)
Preparation of (8) where $R^4$, $R^6$, $R^7$ and $R^9$ are Hydrogen, $R^3$ and $R^5$ are Methyl, and $R^8$ is Isopropyl A solution of 3,5-dimethyl-4-(3'-isopropyl-4'-methoxybenzylhydroxy) anisole (7) (2.0 g, 6.36 mmol) in 22 mL of 9% (v/v) acetic acid in ethanol containing 10% Pd/C (200 mg) was hydrogenated at 1 atmosphere at room temperature. When hydrogen uptake was complete (12 hours), the catalyst was filtered off and the filtrate was diluted with 200 mL of ether, washed with saturated $NaHCO_3$ solution (3×50 mL), water (150 mL) and brine (3×50 mL). The solvent was evaporated to yield 1.5 g (5.03 mmol, 79%) of 3,5-dimethyl-4-(3'-isopropyl-4'-methoxybenzyl) anisole (8) as an oil. This material was used in the next step without further purification; $^1$HNMR ($CDCl_3$) δ 1.2 (d, 6H), 2.23 (s, 6H), 3.27 (heptet, 1H), 3.78 (s, 3H), 3.82 (s, 3H), 3.93 (s, 2H), 6.63 (s, 2H), 6.70 (m, 2H), 6.97 (s, 1H).

Preparation of (8), Varying $R^4$, $R^6$, $R^7$, $R^8$ and $R^9$

In a similar manner, replacing 3,5-dimethyl-4-(3'-isopropyl-4'-methoxybenzylhydroxy) anisole with other compounds of Formula (7), and following the procedure described in Example 6 above, other compounds of Formula (8) are prepared.

EXAMPLE 7

Preparation of Compounds of Formula (9)
Preparation of (9) where $R^4$, $R^6$, $R^7$ and $R^9$ are Hydrogen, $R^3$ and $R^5$ are Methyl, and $R^8$ is Isopropyl To 3,5-dimethyl-4-(3'-isopropyl-4'-methoxybenzyl) anisole (8) (1.3 g, 4.35 mmol) in 75 mL of methylene chloride at −78° C. was added 44 mL of boron tribromide 1.0M in methylene chloride). The reaction mixture was stirred for 30 min at −78° C. and for 10 hours at room temperature. The reaction mixture was washed with water (2×100 mL), dried ($MgSO_4$), and evaporated to give crude product (1.5 g). Purification using flash column chromatography (silica gel, 80:20 hexane/ethylacetate) gave 3,5-dimethyl-4-(4'-hydroxy-3'-isopropylbenzyl) phenol (9) (812 mg, 3.00 mmol, 69%); $^1$HNMR ($CDCl_3$) δ 1.2 (d, 6H), 2.23 (s, 6H), 3.15 (heptet, 1H), 3.87 (s, 2H), 6.58 (m, 4H), 6.92 (s, 1H).

Preparation of (9), Varying $R^4$, $R^6$, $R^7$, $R^8$ and $R^9$

In a similar manner, replacing 3,5-dimethyl-4-(3'-isopropyl-4'-methoxybenzyl) anisole with other compounds of Formula (8), and following the procedure described in Example 7 above, other compounds of Formula (9) are prepared.

EXAMPLE 8

Preparation of Compounds of Formula I
Preparation of I where n is 1, $R^4$, $R^6$, $R^7$, $R^9$, and $R^{10}$ are Hydrogen, $R^3$ and $R^5$ are Methyl, and $R^8$ is Isopropyl To cesium carbonate (3.01 g, 9.24 mmol) and 3,5-dimethyl-4-(4'-hydroxy-3'-isopropylbenzyl) phenol (9) (500 mg, 1.85 mmol) in 37.5 mL of 37% (v/v) DMF in tetrahydrofuran at −25° C. was added tert-butylchloroacetate (278,6 mg, 1.85 mmol). The reaction mixture was stirred for 1 hour at −25° C. and for 30 minutes at room temperature, poured into 100 mL of cold 1N HCl, and extracted with ethyl acetate (3×150 mL). The combined organic portions were dried ($MgSO_4$) and evaporated to yield 700 mg of crude, which was purified using flash column chromatography (silica gel, 90:10 hexane/ethylacetate) to yield the t-butyl ester of [3,5-dimethyl-4-(4'-hydroxy-3'-isopropylbenzyl)-phenoxy] acetic acid (250 mg), used directly in the following reaction; $^1$HNMR ($CDCl_3$) δ 1.2 (d, 6H), 1.5 (s, 9H), 2.23 (s, 6H), 3.15 (heptet, 1H), 3.9 (s, 2H), 4.52 (s, 2H), 6.58 (m, 4H), 6.92 (s, 1H).

To the above ester (200 mg, 0.520 mmol) in 4 mL of methanol was added 2.6 mL of 1N NaOH. The mixture was stirred for 1 hour at room temperature, acidified with 3 mL of 2N HCl, and extracted with ethylacetate (2×25 mL). The combined organic portions were dried ($MgSO_4$) and evaporated to give [3,5-dimethyl-4-(4'-hydroxy-3'-isopropylbenzyl)-phenoxy] acetic acid (10) (170 mg, 0.518 mmol, 28%); $^1$HNMR ($CD_3OD$) δ 1.2 (d, 6H), 2.23 (s, 6H), 3.19 (heptet, 1H), 3.83 (s, 2H), 4.39 (s, 2H), 6.56 (m, 2H), 6.67 (s, 2H) 6.83 (s, 1H).

Preparation of I, Varying n, $R^4$, $R^6$, $R^7$, R8, $R^9$, and $R^{10}$

In a similar manner, replacing 3,5-dimethyl-4-(4'-hydroxy-3'-isopropylbenzyl) phenol with other compounds of Formula (9), and following the procedure described in Example 8 above, other compounds of Formula I are prepared.

EXAMPLE 9

Preparation of Compounds of Formula (10)
Preparation of (10) where $R^4$, $R^6$, $R^7$, and $R^9$ are Hydrogen, $R^3$ and $R^5$ are Methyl, and $R^8$ is Isopropyl To 3,5-dimethyl-4-(3'-isopropyl-4'-methoxybenzylhydroxy) anisole (7) (10 g, 31.80 mmol) in 150 mL of methylene chloride at 0° C. was added pyridinium dichromate, (23.93 g, 63.60 mmol). The reaction mixture was stirred for 4 hours at 0° C. and then filtered through Celite. The filtrate was evaporated, and the residue was purified by flash column chromatography (silica gel, 95:5 hexane/ethylacetate) to give (2,6-dimethyl-4-methoxyphenyl)-(3-isopropyl-4-methoxyphenyl) methanone (10) (6 g, 19.23 mmol, 60%); $^1$ HNMR ($CDCl_3$) δ 1.20 (d, 6H), 2.27 (s, 6H), 3.30 (heptet, 1H), 3.83 (s, 3H), 3.89 (s, 3H), 6.58 (s, 2H), 6.8 (d, 1H), 7.5 (d, 1H), 7.85 (s (1H).

Preparation of (10), Varying $R^4$, $R^6$, $R^7$, R8, $R^9$ and $R^{10}$

In a similar manner, replacing 3,5-dimethyl-4-(3'-isopropyl-4'-methoxybenzylhydroxy) anisole with other compounds of Formula (7), and following the procedure described in Example 9 above, other compounds of Formula (10) are prepared.

EXAMPLE 10

Preparation of Compounds of Formula (11)
Preparation of (11) where $R^1$ is Methyl, $R^4$, $R^6$, $R^7$, and $R^9$ are Hydrogen, $R^3$ and $R^5$ are Methyl, and $R^8$ is Isopropyl To anhydrous cerium chloride (1.185 g, 4.80 mmol) dry tetrahydrofuran (15 mL) was added with stirring under argon and stirring was continued for 2 hours at room temperature. The resultant suspension was then cooled at −78° C., and 3.43 mL of methyllithium (1.4M in diethylether) was added with stirring, whereupon the color of the suspension turned from white to yellow. After maintaining the same temperature for 30 minutes, (2,6-dimethyl-4-methoxyphenyl)-(3-isopropyl-4-methoxyphenyl) methanone (10) (1 g, 3.20 mmol) in tetrahydrofuran (5 mL) was added and the mixture was stirred for 3 hours at −78° C. and for 2 hours at 0° C. The reaction mixture was treated with sat. $NH_4Cl$ solution, filtered through Celite, and extracted with ethyl acetate. The combined extracts were dried ($Na_2SO_4$), evaporated, and the residue was purified by flash column chromatography (silica gel, 97:3 hexane/ethylacetate) to give 1-(2,6-dimethyl-4-methoxyphenyl)-1-(3-isopropyl-4-methoxyphenyl) ethanol (12) (450 mg, 1.37 mmol, 43%); $^1$HNMR ($CDCl_3$) δ 1.20 (dd, 6H), 1.58 (s, 3H), 2.12 (s, 3H), 2.18 (s, 3H), 3.30 (heptet, 1H), 3.82 (s, 3H), 3.88 (s, 3H), 6.50 (s, 1H), 6.60 (s, 2H), 6.80 (d, 1H), 7.06 (d, 1H).

Preparation of (11), Varying $R^4$, $R^6$, $R^7$, R8, $R^9$, and $R^{10}$

In a similar manner, optionally replacing methyllithium with other alkyl lithiums, and optionally replacing (2,6-dimethyl-4-methoxyphenyl)-(3-isopropyl-4-methoxyphenyl) methanone with other compounds of Formula (10), and following the procedure described in Example 10 above, other compounds of Formula (11) are prepared.

EXAMPLE 11

Preparation of Compounds of Formula (12)
Preparation of (12) where $R^1$ is Methyl, $R^4$, $R^6$, $R^7$, and $R^9$ are Hydrogen, $R^3$ and $R^5$ are Methyl, and $R^8$ is Isopropyl A solution of 1-(2,6-dimethyl-4-methoxyphenyl)-1-(3-isopropyl-4-methoxyphenyl) ethanol (400 mg, 1.218 mmol) in 4.4 mL of 9% (v/v) AcOH in EtOH containing 10% Pd/C (40 mg) was hydrogenated at 1 atm at room temperature. When hydrogen uptake was complete (12 hours), the catalyst was filtered off and the filtrate was diluted with 50 mL of ether, washed with sat. $NaHCO_3$ solution (3×10 mL), water (30 mL) and brine (3×10 mL). The solvent was evaporated to yield 300 mg (0.96 mmol, 79%) of 1-(2,6-dimethyl-4-methoxyphenyl)-1-(3-isopropyl-4-methoxyphenyl) ethane as an oil. This material was used in the next step without further purification; $^1$HNMR ($CDCl_3$) & 1.16 (dd, 6H), 1.63 (d, 3H), 2.12 (s, 6H), 3.27 (heptet, 1H), 3.81 (s, 6H), 4.54 (q, 1H), 6.54 (s, 2H), 6.75 (d, 1H), 6.88 (d, 1H), 7.04 (s, 1H).
Preparation of (12), Varying $R^4$, $R^6$, $R^7$, R8, $R^9$, and $R^{10}$ In a similar manner, replacing 1-(2,6-dimethyl-4-methoxyphenyl)-1-(3-isopropyl-4-methoxyphenyl) ethanol with other compounds of Formula (11), and following the procedure described in Example 11 above, other compounds of Formula (12) are prepared.

EXAMPLE 12

Preparation of Compounds of Formula I
Preparation of I where n is 1, $R^1$ is Hydrogen, $R^2$ is Methyl, $R^4$, $R^6$, $R^7$, $R^9$, and $R^{10}$ are Hydrogen, $R^3$ and $R^5$ are Methyl, and $R^8$ is Isopropyl A. To 1-(2,6-dimethyl-4-methoxyphenyl)-1-(3-isopropyl-4-methoxyphenyl) ethane (250 mg, 0.8 mmol) in 15 mL of methylene chloride at −78° C. was added 8 mL of boron tribromide (1.0M in methylene chloride). The reaction mixture was stirred for 30 minutes at −78° C. and for 20 hours at room temperature. The reaction mixture was washed with water (2×25 mL), dried ($MgSO_4$), and evaporated to give crude product (300 mg). Purification using flash column chromatography (silica gel, 90:10 hexane/ethylacetate) gave 1-(4-hydroxy-2,6-dimethylphenyl)-1-(4-hydroxy-3-isopropylphenyl) ethane (160 mg, 0.562 mmol, 70%); $^1$HNMR ($CDCl_3$) δ 1.20 (dd, 6H), 1.60 (d, 3H), 2.25 (s, 6H), 2.35 (s, 3H), 3.20 (heptet, 1H), 4.45 (q, 1H), 6.45 (s, 1H), 6.65 (m, 2H), 7.00 (d, 1H), 7.20 (d, 1H).

B. To cesium carbonate (801.5 mg, 2.46 mmol) and 1-(4-hydroxy-2,6-dimethylphenyl)-1-(4-hydroxy-3-isopropylphenyl) ethane (140 mg, 0.492 mmol) in 10 mL of 37% (v/v) in tetrahydrofuran at −25° C. was added tert-butylchloroacetate (74.1 mg, 0.492 mmol). The reaction mixture was stirred for 1 hour at −25° C. and for 30 minutes at room temperature, poured into 30 mL of cold 1N HCl, and extracted with ethyl acetate (3×50 mL). The combined organic portions were dried ($MgSO_4$) and evaporated to yield 200 mg of crude, which was purified using flash column chromatography (90:10), hexane/ethylacetate) to yield {3,5-dimethyl-4-[(4'-hydroxy-3'-isopropylphenyl) ethane]phenoxy}acetic acid t-butyl ester (80 mg), used in the following reaction; $^1$HNMR ($CDCl_3$) δ 1.20 (dd, 6H), 1.46 (s, 9H), 1.67 (d, 3H), 2.19 (s, 3H), 2.24 (s, 2H), 3.15 (heptet, 1H), 4.25 (q, 2H), 4.60 (q, 1H), 6.40 (s, 2H), 6.58 (s, 2H) 6.91 (d, 1H), 7.11 (d, 1H).

C. To the above ester (70 mg, 0.176 mmol) in 1.4 mL of methanol was added 0.90 mL of 1N NaOH. The reaction mixture was stirred for 1 hour at room temperature, acidified with 1 mL of 2N HCl, and extracted with ethyl acetate (2×15 mL). The combined organic portions were dried ($MgSO_4$) and evaporated to give {3,5-dimethyl-4-[(4'-hydroxy-3'-isopropylphenyl)ethane]phenoxy}acetic acid (50 mg, 0.146 mmol, 30%); $^1$HNMR ($CD_3OD$) δ 1.13 (dd, 6H), 1.60 (d, 3H), 2.04 (s, 3H), 2.20 (2, 3H), 3.20 (heptet, 1H), 4.16 (s, 2H), 4.71 (q, 1H), 6.6 (m, 3H), 6.70 (d, 1H), 6.97 (s, 1H).
Preparation of I, Varying n, $R^4$, $R^6$, $R^7$, R8, $R^9$, and $R^{10}$ In a similar manner, replacing 1-(2,6-dimethyl-4-methoxyphenyl)-1-(3-isopropyl-4-methoxyphenyl) ethane with other compounds of Formula (12), and following the procedure described in Example 12 above, steps A, B and C above, other compounds of Formula I are prepared.

EXAMPLE 13

Preparation of Compounds of Formula I
Preparation of I where n is 1, $R^1$ and $R^2$ taken together with the Carbon to which they are attached represent $-C=O$, $R^4$, $R^6$, $R^7$ and $R^9$ are Hydrogen, $R^{10}$ is Methyl, $R^3$ and $R^5$ are Methyl, and $R^8$ is Isopropyl To (2,6-dimethyl-4-methoxyphenyl)-(3-isopropyl-4-methoxyphenyl) methanone (10) (1 g, 3.20 mmol) in 60 ml of methylene chloride at −78° C. was added 32 mL of boron tribromide (1.0M in methylene chloride). The reaction mixture was stirred at −78° C. for 30 minutes, and then for 12 hours at room temperature. The reaction mixture was washed with water (2×125 mL), dried ($MgSO_4$), and evaporated to give crude product (900 mg). Purification using flash column chromatography (silica gel, 90:10 hexane/ethylacetate) gave 3,5-dimethyl-4-(4'-methoxy-3'-isopropylbenzoyl) phenol (13) (300 mg, 31%) and 3,5-dimethyl-4-(4'-hydroxy-3'-isopropylbenzyl) phenol (14) (450 mg, 49%).

Using the procedure described in Example 8:

1. The compound of Formula (13) was converted to [3,5-dimethyl-4-(4'-methoxy-3'-isopropylbenzoyl) phenoxy[acetic acid (100 mg, 49%); $^1$HNMR ($CD_3OD$) δ 1.18 (d, 6H), 2.05 (s, 6H), 3.20 (heptet, 1H), 3.90 (s, 2H), 4.46 (s, 2H), 6.70 (s, 2H), 6.90 (d, 1H), 7.43 (d, 1H), 7.81 (s, 1H).

2. The compound of Formula (14) was converted to a mixture of two compounds that were separated by chromatography;

[3,5-dimethyl-4-(4'-hydroxy-3'-isopropylbenzoyl) phenoxy[acetic acid (100 mg, 27%);
$^1$HNMR ($CD_3OD$) δ 1.2 (d, 6H), 2.07 (s, 6H), 3.36 (heptet, 1H), 4.46 (s, 2H), 6.67 (s, 2H), 6.75 (d, 1H), 7.40 (d, 1H), 7.73 (s, 1H); and

[2-isopropyl-4-(4'-hydroxy-2',6'-dimethylbenzyl) phenoxy]acetic acid; $^1$HNMR ($CD_3OD$) δ 1.18 (d, 6H), 1.94 (s, 6H), 3.46 (heptet, 1H), 4.56 (s, 2H), 6.51 (s, 2H), 6.84 (d, 1H), 7.46 (d, 1H), 7.76 (s, 1H).
Preparation of I, Varying n, $R^6$, $R^7$, R8, $R^9$, and $R^{10}$ In a similar manner, replacing (2,6-dimethyl-4-methoxyphenyl)-(3-isopropyl-4-methoxyphenyl) methanone with other compounds of Formula (10), and following the procedure described in Example 13 above, other compounds of Formula I are prepared.

EXAMPLE 14

Preparation of Compounds of Formula I

Preparation of I where n is 1, $R^1$, and $R^2$ taken together with the Carbon to which they are attached represent –C=O, $R^4$, $R^7$ and $R^9$ are Hydrogen, $R^6$ is n-Butyl, $R^{10}$ is Methyl, $R^3$ and $R^5$ are Methyl, and $R^8$ is Isopropyl To anhydrous cerium chloride (3.16 g, 12.8 mmol) dry tetrahydrofuran (50 mL) was added with stirring under argon and stirring was continued for 2 hours at room temperature. The resultant suspension was then cooled to –78° C., and 6.4 mL of n-butyllithium (2.0M in pentane) was added with stirring, whereupon the color of the suspension turned from white to yellow. After maintaining the same temperature for 30 minutes, (2,6-dimethyl-4-methoxyphenyl)-(3-isopropyl-4-methoxyphenyl) methanone (10) (1 g, 3.20 mmol) in tetrahydrofuran (5 mL) was added and the mixture was stirred for 3 hours at –78° C. and for 2 hours at 0° C. The reaction mixture was treated with sat. $NH_4Cl$ solution, filtered through Celite, and extracted with ethyl acetate. The combined extracts were dried ($Na_2SO_4$), evaporated, and the residue was purified by flash column chromatography (silica gel, 95:5 hexane/ethylacetate) to give (2,6-dimethyl-4-methoxyphenyl)-(6-n-butyl-3-isopropyl-4-methoxyphenyl) methanone (15) (500 mg, 43%); $^1$HNMR ($CDCl_3$) δ 0.98 (t, 3H), 1.03 (d, 6H), 1.41 (m, 2H), 1.59 (m, 2H), 2.09 (s, 6H), 3.05 (t, 2H), 3.14 (heptet, 1H),3.86 (d, 6H), 6.52 (d, 2H), 6.73 (s, 2H), 7.22 (s, 1H).

Using the procedure described in Example 12, compound (15) was converted to (2,6-dimethyl-4-hydroxyphenyl)-(6-n-butyl-3-isopropyl-4-hydroxyphenyl) methanone (200 mg, 54%); $^1$HNMR ($CDCl_3$) δ 0.93 (t, 3H), 1.08 (d, 6H), 1.39 (m, 2H), 1.61 (m, 2H), 2.06 (s, 6H), 2.98 (t, 2H), 3.07 (heptet, 1H), 6.50 (s, 2H), 6.65 (s, 2H), 7.24 (s, 1H).

Using the procedure described in Example 8, the above dihydroxy compound was converted to a mixture of three compounds that were separated by chromatography;

1. [3,5-dimethyl-4-(4'-hydroxy-3'-isopropyl-6'-n-butylbenzoyl)phenoxy [acetic acid (25 mg, 14%); $^1$HNMR ($CD_3OD$) δ 0.98 (t,3H), 1.01 (d, 6H), 1.43 (m, 2H), 1.61 (m, 2H), 2.07 (s, 6H), 2.98 (t, 2H), 3.13 (heptet, 1H), 4.22 (s, 2H), 6.66 (s, 2H), 7.19 (s, 1H), 7.84 (s, 1H);

2. [2-Isopropyl-4-(4'-hydroxy-2',6'-dimethylbenzoyl)-6-n-butylphenoxy]acetic acid (20 mg, 11%); $^1$HNMR ($CD_3OD$) δ 0.94 (t,3H), 1.05 (d, 6H), 1.40 (m, 2H), 1.59 (m, 2H), 1.99 (s, 6H), 2.98 (t, 2H), 3.29 (heptet, 1H), 4.51 (s, 2H), 6.50 (s, 2H), 6.70 (s, 1H), 7.25 (s, 1H); and 3. [3,5-dimethyl-4-(4'-oxyacetic-3'-isopropyl-6'-n-butylbenzoyl)phenoxy[acetic acid (30 mg, 15%); $^1$HNMR ($CD_3OD$) δ 0.97 (t,3H), 1.02 (d, 6H), 1.46 (m, 2H), 1.62 (m, 2H), 1.96 (s, 6H), 3.04 (t, 2H), 3.32 (heptet, 1H), 4.51 (s, 4H), 6.68 (s, 2H), 6.78 (s, 1H), 7.24 (s, 1H).

Preparation of I, Varying n, $R^4$, $R^6$, $R^7$, R8, $R^9$, and $R^{10}$

In a similar manner, replacing (2,6-dimethyl-4-methoxyphenyl)-(3-isopropyl-4-methoxyphenyl) methanone with other compounds of Formula (10), and following the procedure described in Example 14 above, other compounds of Formula I are prepared.

EXAMPLE 15

This example illustrates the preparation of a representative pharmaceutical formulation for oral administration containing an active compound of Formula I, e.g. [3,5-dimethyl-4-(4'-hydroxy-3'-isopropylbenzyl)-phenoxy] acetic acid.

| Ingredients | Quantity per tablet, mgs. |
|---|---|
| Active Compound | 200 |
| Lactose, spray-dried | 148 |
| Magnesium stearate | 2 |

The above ingredients are mixed and introduced into a hard-shell gelatin capsule.

Other compounds of Formula I can be used as the active compound in the preparation of the orally administrable formulations of this example.

EXAMPLE 16

This example illustrates the preparation of another representative pharmaceutical formulation for oral administration containing a compound of Formula I, e.g., [3,5-dimaethyl-4-(4'-hydroxy-3'-isopropylbenzyl)-phenoxy] acetic acid.

| Ingredients | Quantity per tablet, mgs. |
|---|---|
| Active Compound | 400 |
| Cornstarch | 50 |
| Lactose | 145 |
| Magnesium stearate | 5 |

The above ingredients are mixed intimately and pressed into single scored tablets.

Other compounds of Formula I can be used as the active compound in the preparation of the orally administrable formulations of this example.

EXAMPLE 17

This example illustrates the preparation of a representative pharmaceutical formulation containing a compound of Formula I, e.g., [3,5-dimethyl-4-(4'-hydroxy-3'-isopropylbenzyl)-phenoxy] acetic acid An oral suspension is prepared having the following composition.

| Ingredients | |
|---|---|
| Active Compound | 1.0 g |
| Fumaric acid | 0.5 g |
| Sodium chloride | 2.0 g |
| Methyl paraben | 0.1 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

Other compounds of Formula I can be used as the active compound in the preparation of the orally administrable formulations of this example.

EXAMPLE 18

This example illustrates the preparation of a representative pharmaceutical formulation for oral administration containing an active compound of Formula I, e.g. [3,5-dimethyl-4-(4'-hydroxy-3'-isopropylbenzyl)-phenoxy] acetic acid An injectable preparation buffered to a pH of 4 is prepared having the following composition:

| Ingredients | |
| --- | --- |
| Active Compound | 0.2 g |
| Sodium Acetate Buffer Solution (0.4 M) | 2.0 ml |
| HCL (1N) | q.s. to pH 4 |
| Water (distilled, sterile) | q.s. to 20 ml |

Other compounds of Formula I can be used as the active compound in the preparation of the injectable formulations of this example.

EXAMPLE 19

This example illustrates the preparation of a representative pharmaceutical formulation for topical application containing a compound of Formula I, e.g., [3,5-dimethyl-4-(4'-hydroxy-3'-isopropylbenzyl)-phenoxy] acetic acid.

| Ingredients | grams |
| --- | --- |
| Active compound | 0.2–10 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. to 100 |

All of the above ingredients, except water, are combined and heated to 60° C. with stirring. A sufficient quantity of water at 60° C. is then added with vigorous stirring to emulsify the ingredients, and water then added q.s. 100 g.

Other compounds of Formula I can be used as the active compound in the preparation of the topical formulations of this example.

EXAMPLE 20

This example illustrates the preparation of a representative pharmaceutical formulation containing a compound of Formula I, e.g., [3,5-dimethyl-4-(4'-hydroxy-3'-isopropylbenzyl)-phenoxy] acetic acid.

A suppository totalling 2.5 grams is prepared having the following composition:

| Ingredients | |
| --- | --- |
| Active Compound | 500 mg |
| Witepsol H-15* | balance |

(*triglycerides of saturated vegetable fatty acid; a product of Riches-Nelson, Inc., New York, N.Y.)

Other compounds of Formula I can be used as the active compound in the preparation of the suppository formulations of this example.

EXAMPLE 21

Receptor Binding Assays of TR Ligands

To test the ability of synthesized TR ligands to bind to a thyroid receptor (TR), the binding affinity of a TR ligand for TR is assayed using TR's expressed in *E Coli* and $125_I$ $T_3$ using the method described by Apriletti et al., *Protein Expression and Purification*, 6:363–370 (1995), and by Apriletti et al., *J. Biol. Chem.* (1988) which is incorporated by reference herein. The TR binding experiment is conducted using the recombinant TRs in the presence of the sample to be assayed, 1 nM [$^{125}$I]$T_3$, and 50 µg/ml core histones, in buffer E (400 mM KCl, 200 mM potassium phosphate, pH 8.0, 0.5 mM EDTA, 1 mM $MgCl_2$, 10% glycerol, 1 mM DTT) in a volume of 0.21 ml. After incubation overnight at 4° C., 0.2 ml of the incubation mixture is loaded onto a Quick-Sep Sephadex G-25 column (2.7×0.9 cm, 1.7 ml bed volume) equilibrated with buffer E. The excluded peak of protein-bound [$^{125}$I]$T_3$ is eluted with 1 ml of buffer E, collected in a test tube, and counted. Specific $T_3$ binding is calculated by subtracting nonspecific binding from total binding. $IC_{50}$ values correspond to the concentration of test ligand required to displace 50% of [$^{125}$I]$T_3$ from the TR.

| $IC_{50}$ T3 [nM] | | $IC_{50}$ GC1 [nM] | |
| --- | --- | --- | --- |
| TR $\beta_1$ | TR $\alpha_1$ | TR $\beta_1$ | TR $\alpha_1$ |
| 2.8 | 1.5 | 2.5 | 20 |

T3 is (3,5,3'-triiodo-L-thyronine).
GC1 is [3,5-dimethyl-4-(4'-hydroxy-3'-isopropylbenzyl)-phenoxy] acetic acid.

EXAMPLE 22

Cellular Transcription Assay of TR Ligands Cell Culture, Transfections and Luciferase Assay Cellular transactivation assays were performed according to the procedure in Ribeiro R. C. et al. (1996) *J. Biol. Chem.* 271, 17147–17151. Briefly, HeLa cells were grown in 15 cm dishes in DME H-21, 4.5 g/L glucose with 10% newborn bovine serum, 2 mM glutamine, 50 units/ml penicillin, and 50 µg/ml streptomycin.

For transfections, cells were trypsinized, resuspended in buffer (PBS, 0.1% glucose), and mixed with the reporter gene and with the appropriate thyroid receptor (TR) expression vectors (CMV TR $\beta_1$, CMV TR $\alpha_1$). The reporter gene consisted of a synthetic TR response element (DR-4) containing two copies of a direct repeat spaced by four nucleotides (AGGTCA-caggAGGTCA) cloned in the HindIII site of the pUC19 polylinker immediately upstream of a minimal (−32/+45) thymidine kinase promoter linked to luciferase coding sequences.

Cells in 0.5 ml of buffer (8+/−2 million cells) were electroporated using a Bio-Rad gene pulser at 0.35 kvolts and 960 microfarads. After electroporation, cells were pooled in growth medium (DME H-21 with 10% charcoal-treated, hormone stripped, newborn bovine serum), plated in 6-well dishes, and treated with either vehicle (ethanol), hormone ($T_3$), or $T_3$ analog ($GC_1$). $T_3$ and $GC_1$ were used at increasing concentrations, $10^{-10}$M to $10^{-7}$M and $10^{-11}$M to $10^{-5}$M, respectively. After incubation at 37° C. for 24 hours, incubation media was discarded and the cells were detached with 1 ml of calcium/magnesium-free PBS, 1 mM EDTA, prewarmed at 37° C., and transferred to 1.5 ml Eppendorf tubes. Cells were pelleted by centrifugation in a microfuge for 1 minute at room temperature. The supernatants were aspirated and the pellets lysed by addition of 120 µl of Tris-Cl 0.25M pH 7.6, 0.1% Triton. After resuspension by vortexing for 5–10 sec, the lysates were pelleted by centrifugation in a microfuge for 5 min at room temperature. One hundred μl of each Eppendorf tube lysate was added to 300 μl of 25 mM glycylglycine pH 7.8, 15 mM MgSO$_4$, 4 mM EGTA, 15 mM potassium phosphate pH 7.8, 1 mM DTT, 2 mM ATP, and 0.2 mM Luciferine. The light output was measured for 10 sec at room temperature with a luminometer (Analytical Luminescence Laboratory, MONOLIGHT® 1500).

The concentration of T$_3$ or GC$_1$ required for half-maximal induction of Luciferase activity (EC$_{50}$) was calculated using a curve fitting program.

Results of Testing

| Experiment | EC$_{50}$ T$_3$ [nM] | | EC$_{50}$ GC$_1$ [nM] | |
|---|---|---|---|---|
| | TRβ$_1$ | TRα$_1$ | TRβ$_1$ | TRα$_1$ |
| 1 | 1.34 | 0.25 | 5.02 | 22.99 |
| 2 | 1.42 | 0.33 | 12.68 | 36.79 |
| 3 | 0.80 | 0.44 | 2.14 | 16.97 |

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

APPENDIX I

Andrea, T. A., et al. *J Med Chem* 22, 221–232 (1979).
Andrews et al, U.S. Pat. No. 4,741,897, issued May 3, 1989.
Apriletti, J. W., Baxter, J. D., Lau, K. H & West, B. L. *Protein Expression and Purification* 6, 363–370 (1995).
Apriletti, J. W., Baxter, J. D. & Lavin, T. N. *J. Biol. Chem.* 263, 9409–9417 (1988).
Au-Fliegner, M., Helmer, E., Casanova, J., Raaka, B. M. & Samuels, H. H. *Mol Cell Biol* 13, 5725–5737 (1993).
Baniahmad, A., et al. *Mol Cell Biol* 15, 76–86 (1995).
Barettino, D., Vivanco Ruiz, M. M. & Stunnenberg, H. G. *Embo J* 13, 3039–3049 (1994).
Beck-Peccoz, P., et al. *J Clin Endocrinol Metab* 78, 990–993 (1994).
Bhat, M. K., McPhie, P. & Cheng, S. Y. *Biochem Biophys Res Commun* 210, 464–471 (1995).
Blake, C. C. & Oatley, S. J. *Nature* 268, 115–120 (1977).
Blake, C. C., Geisow, M. J., Oatley, S. J., Rerat, B. & Rerat, C. *J Mol Biol* 121, 339–356 (1978).
Bourguet, W., Ruff, M., Chambon, P., Gronemeyer, H. & Moras, D. *Nature* 375, 377–382 (1995).
Brent, G. A. *N Engl J Med* 331, 847–853 (1994).
Brunger, A. T., Kuriyan, J. & Karplus, M. *Science* 235, 458–460 (1987).
Casanova, J., et al. *Mol Cell Biol* 14, 5756–5765 (1994).
Cavailles, V., et al. *Embo J* 14, 3741–3751 (1995).
Chin et al, U.S. Pat. No. 5,284,999, issued Feb. 8, 1994.
Collaborative Computational Project, N.4. *Acta Crystallogr.* D50, 760–763 (1994).
Collingwood, T. N., Adams, M., Tone, Y & Chatterjee, V. K. *Mol Endocrinol* 8, 1262–1277 (1994).
Cowtan, K. *Joint CCP4 and ESF-EACBM Newsletter on Protein Crystallography* 31, 34–38 (1994).
Damm, K. & Evans, R. M. *Proc Natl Acad Sci U S A* 90, 10668–10672 (1993).
Danielian, P. S., White, R., Lees, J. A. & Parker, M. G. *Embo J* 11, 1025–1033 (1992).
Davies et al, U.S. Pat. No. 5,322,933, issued Jun. 21, 1994.
DeGroot et al, U.S. Pat. No. 5,438,126, issued Aug. 1, 1995.
Dietrich, S. W., Bolger, M. B., Kollman, P. A. & Jorgensen, E. C. *J Med Chem* 20, 863–880 (1977).
Durand, B., et al. *Embo J* 13, 5370–5382 (1994).
Ellis et al, U.S. Pat. No. 4,766,121, issued Aug. 23, 1988.
Ellis et al, U.S. Pat. No. 4,910,305, issued Mar. 20, 1990.
Emmett et al, U.S. Pat. No. 5,061,798, issued Oct. 29, 1991.
Evans, R. M. *Science* 240, 889–895 (1988).
Evans et al, U.S. Pat. No. 5,171,671, issued Dec. 15, 1992.
Evans et al, U.S. Pat. No. 5,312,732, issued May 17, 1994.
Fawell, S. E., Lees, J. A., White, R. & Parker, M. G. *Cell* 60, 953–962 (1990).
Forman, B. M. & Samuels, H. H. *Mol. Endocrinol.* 4, 1293–1301 (1990).
Gewirth, D. T. & Sigler, P. B. *Nature Structural Biology* 2, 386–394 (1995).
Glass, C. K. *Endocr Rev* 15, 391–407 (1994).
Hayashi, Y. Sunthornthepvarakul, T. & Refetoff, S. *J Clin Invest* 94, 607–615 (1994).
Jones, T. A., Zou, J. Y., Cowan, S. W. & Kjeldgaard. *Acta Crystallogr A* 47, 110–119 (1991).
Jorgensen, E. C., *J Med Chem* 17, 434–439 (1974).
Kabsch, W. *J. Appl. Crystallogr.* 26, 795–800 (1993).
Kabsch, W. & Sander, C. *Biopolymers* 22, 2577–2637 (1983).
Kollman, P. A., JACS 95:26, 8518–8525 (1973).
Laskowski, R. A., Macarthur, M. W., Moss, D. S. & Thornton, J. M. *J. Appl. Crystallogr.* 26, 283–291 (1993).
Latham, K. R., Apriletti, J. W., Eberhardt, N. L. & Baxter, J. D. *J Biol Chem* 256, 12088–12093 (1981).
Laudet, V., Hanni, C., Coll, J., Catzeflis, F. & Stehelin, D. *Embo J* 11, 1003–1013 (1992).
LeDouarin, B., et al. *Embo J* 14, 2020–2033 (1995).
Lee, J. W., Ryan, F., Swaffield, J. C., Johnston, S. A. & Moore, D. D. *Nature* 374, 91–94 (1995).
Lee, J. W., Choi, H. S., Gyuris, J., Brent, R. & Moore, D. D. *Molec. Endocrinol.* 9, 243–254 (1995).
Leeson, P. D., Emmett, J. C., Shah, V. P., Showell, G. A., Novelli, R., Prain, H. D., Benson, M. G., Ellis, D., Pearce, N. J. & Underwood, A. H. *J. Med. Chem.* 32, 320–336 (1989).
Leeson, P. D., Ellis, D., Emmett, J. D., Shah, V. P., Showell, G. A. & Underwood, A. H. J. Leng, X., et al. *Mol Cell Biol* 15, 255–263 (1995).
Leng, X., Tsai, S. Y., O'Malley, B. W. & Tsai, M. J. *J Steroid Biochem Mol Biol* 46, 643–661 (1993).
Lin, K. H., Parkison, C., McPhie, P. & Cheng, S. Y. *Mol. Endocrinol.* 5, 485–492 (1991).
Luisi, B. F., et al. *Nature* 352, 497–505 (1991).
McGrath, M. E., et al. *J. Mol. Biol.* 237, 236–239 (1994).
Meier, C. A., et al. *Mol. Endocrinol.* 6, 248–258 (1992).
Miura et al, U.S. Pat. No. 5,116,828, issued May 26, 1992.
Monaco, H. L., Rizzi, M. & Coda, A. *Science* 268, 1039–1041 (1995).
Nicholls, A., Sharp, K. A. & Honig, B. *Proteins* 11, 281–296 (1991).
O'Donnell, A. L., Rosen, E. D., Darling, D. S. & Koenig, R. J. *Mol. Endocrinol.* 5, 94–99 (1991).
Ozato, U.S. Pat. No. 5,403,925, issued April 4, 1995.
Rastinejad, R., Perlmann, T., Evans, R. M. & Sigler, P. B. *Nature* 375, 203–211 (1995).
Refetoff, S., Weiss, R. E. & Usala, S. J. *Endocr. Rev.* 14, 348–399 (1993).

Ribeiro, R. C. J., Kushner, P. J. & Baxter, J. D. *Annu. Rev. Med.* 46, 443–453 (1995).
Ribeiro, R. C. J., et al. *Ann. N. Y. Acad. Sci.* 758, 366–389 (1995).
Ribeiro, R. C., Kushner, P. J., Apriletti, J. W., West, B. L. & Baxter, J. D. *Mol. Endocrinol.* 6, 1142–1152 (1992).
Saatcioglu, F., Bartunek, P., Deng, T., Zenke, M. & Karin, M. *Mol. Cell Biol.* 13, 3675–3685 (1993).
Schwabe, J. W., Chapman, L., Finch, J. T. & Rhodes, D. *Cell* 75, 567–578 (1993).
Selmi, S. & Samuels, H. H. *J. Biol. Chem.* 266, 11589–11593 (1991).
Swaffield, J. C., Melcher, K. & Johnston, S. A. *Nature* 374, 88–91 (1995).
Toney, J. H. et al. *Biochemistry* 32, 2–6 (1993).
Tsai, M. J. & O'Malley, B.W. *Annu. Rev. Biochem.* 63, 451–486 (1994).
Tripp, S. L. et al., *J. Med. Chem.*, 16, 60–64.
Witte, E-C, et al, Canadian Patent Application 2,169,187.
Zenke, M., Munoz, A., Sap, J., Vennstrom, B. & Beug, H. *Cell* 61, 1035–1049 (1990).

What is claimed is:

1. A compound of the formula:

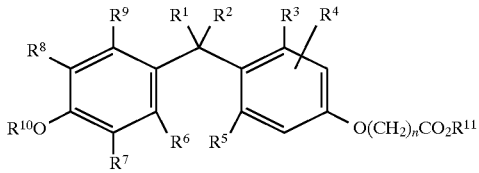

wherein:

n is 1, 2 or 3;

$R^1$ and $R^2$ are independently hydrogen or lower alkyl; or $R^1$ and $R^2$ when taken together with the carbon to which they are attached represent —CHOH, —C=O or —C=S;

$R^3$ and $R^5$ are methyl;

$R^4$ is hydrogen, lower alkyl, or cycloalkyl;

$R^6$ and $R^9$ are hydrogen or lower alkyl;

$R^7$ and $R^8$ are independently hydrogen, lower alkyl, optionally substituted phenyl, optionally substituted benzyl, or heteroaryl;

with the proviso that $R^7$ and $R^8$ cannot both be hydrogen;

$R^{10}$ is hydrogen, lower alkyl, cycloalkyl, or acyl; and $R^{11}$ is hydrogen, lower alkyl, or cycloalkyl;

or a pharmaceutically acceptable salt thereof.

2. The compound of claim 1, wherein $R^4$, $R^6$, $R^7$ and $R^9$ are all hydrogen.

3. The compound of claim 2, wherein $R^{10}$ and $R^{11}$ are hydrogen and n is 1.

4. The compound of claim 3, wherein $R^8$ is lower alkyl.

5. The compound of claim 4, wherein $R^8$ is isopropyl.

6. The compound of claim 5, wherein $R^1$ and $R^2$ are both hydrogen, namely [3,5-dimethyl-4-(4'-hydroxy-3'-isopropylbenzyl)-phenoxy] acetic acid.

7. The compound of claim 5, wherein R is hydrogen and $R^2$ is methyl, namely {3,5-dimethyl-4-[(4'-hydroxy-3'-isopropylphenyl)ethane]phenoxy}acetic acid.

8. The compound of claim 5, wherein $R^1$ and $R^2$ taken together with the carbon to which they are attached represent —C=O, namely [GC3].

9. A pharmaceutical composition for administration to a mammal having a disease state which is alleviated by treatment with a thyroid hormone agonist, which comprises a therapeutically effective amount of a compound of claim 1 in admixture with one or more pharmaceutically acceptable excipients.

10. A method of treating a mammal having a disease state which is alleviated by treatment with a thyroid hormone agonist, which method comprises administering a therapeutically effective amount of a compound of claim 1 to a mammal in need thereof.

11. The method of claim 10, wherein the disease state is hypercholesterolemia.

12. The method of claim 10, wherein the disease state is atherosclerosis.

13. The method of claim 10, wherein the disease state is obesity.

14. The method of claim 10, wherein the disease state is cardiac arrhythmia.

15. The method of claim 10, wherein the disease state is hypothyroidism.

16. The method of claim 10, wherein the disease state is osteoporosis.

17. The method of claim 10, wherein the disease state is depression.

* * * * *

UNITED STATES PATENT AND TRADEMARK OFFICE
CERTIFICATE OF CORRECTION

PATENT NO. : 5,883,294
DATED : March 16, 1999
INVENTOR(S) : Thomas S. Scanlan, Grazia Chiellini, Hikari Yoshihara, James Apriletti, John D. Baxter, Ralff C.J. Ribeiro It is certified that error appears in the above-identified patent and that said Letters Patent is hereby corrected as shown below:

Please correct column 1, line 3, by inserting after "SELECTIVE THYROID HORMONE ANALOGS" and before "INTRODUCTION", the following text:

-- This invention was made with Government support under Grant No. GM50672, awarded by the National Institutes of Health. The Government has certain rights in this invention.--

Signed and Sealed this

Fourteenth Day of September, 1999

Attest:

Q. TODD DICKINSON

*Attesting Officer*  *Acting Commissioner of Patents and Trademarks*

UNITED STATES PATENT AND TRADEMARK OFFICE
CERTIFICATE OF CORRECTION

PATENT NO.   : 5,883,294
DATED        : March 16, 1999
INVENTOR(S)  : Scanlan et al.

It is certified that error appears in the above-identified patent and that said Letters Patent is hereby corrected as shown below:

<u>Title page,</u>
Item [73], the assignee is missing from the patent and should be inserted as follows:

-- The Regents of the University of California --

Signed and Sealed this

Twenty-first Day of January, 2003

JAMES E. ROGAN
*Director of the United States Patent and Trademark Office*

UNITED STATES PATENT AND TRADEMARK OFFICE
CERTIFICATE OF CORRECTION

PATENT NO.   : 5,883,294
DATED        : March 16, 1999
INVENTOR(S)  : Scanlan, Thomas S. et al.

It is certified that error appears in the above-identified patent and that said Letters Patent is hereby corrected as shown below:

Column 17,
Line 62, replace "{3,5-dimethyl-4-[(4'-hydroxy-3'-isopropylphenyl)" with
-- {3,5-dimethyl-4-[1-(4'-hydroxy-3'-isopropylphenyl) --
Line 63, replace "ethane]phenoxy}acetic" with -- ethyl]phenoxy}acetic --

Column 18,
Line 6, replace "{3,5-dimethyl-4-[(4'-hydroxy-3'-" with
-- {3,5-dimethyl-4-[1-(4'-hydroxy-3'- --
Line 7, replace "isopropylphenyl)ethane]phenoxy}acetic" with
-- isopropylphenyl)ethyl]phenoxy}acetic --

Column 26,
Line 13, replace "Ris" with -- $R^1$ is --
Lines 14-15, replace "{3,5-dimethyl-4-[(4'-hydroxy-3'-isopropylphenyl)ethane]phenoxy}acetic acid" with -- {3,5-dimethyl-4-[1-(4'-hydroxy-3'-isopropylphenyl)ethyl]phenoxy}acetic acid --

Signed and Sealed this

Thirteenth Day of May, 2003

JAMES E. ROGAN
*Director of the United States Patent and Trademark Office*